United States Patent
Moldenhauer

(10) Patent No.: US 7,312,207 B2
(45) Date of Patent: Dec. 25, 2007

(54) TOPICAL STEROID CREAM FORMULATIONS

(75) Inventor: Maxine G. Moldenhauer, Acton (CA)

(73) Assignee: Taro Pharmaceuticals North America, Inc., Hawthorne, NY (US)

( * ) Notice: Subject to any disclaimer, the term of this patent is extended or adjusted under 35 U.S.C. 154(b) by 0 days.

(21) Appl. No.: 10/849,282

(22) Filed: May 19, 2004

(65) Prior Publication Data

US 2004/0248866 A1  Dec. 9, 2004

(51) Int. Cl.
*A61K 33/56* (2006.01)

(52) U.S. Cl. ...................... 514/182; 514/172

(58) Field of Classification Search ................. 514/172
See application file for complete search history.

(56) References Cited

U.S. PATENT DOCUMENTS

| | | | |
|---|---|---|---|
| 4,775,529 A | 10/1988 | Sequeira et al. | |
| 4,808,610 A | 2/1989 | Munayyer et al. | |
| 5,422,361 A | 6/1995 | Munayyer et al. | |
| 5,696,105 A * | 12/1997 | Hackler | 514/172 |

* cited by examiner

*Primary Examiner*—San-Ming Hui
(74) *Attorney, Agent, or Firm*—Venable LLP; Michael A. Gollin; Zayd Alathari

(57) ABSTRACT

Disclosed is a novel mometasone furoate cream formulation for topical administration in a oleaginous base containing propylene glycol. This cream is a cosmetically elegant preparation of mometasone that is both stable and bioeffective.

9 Claims, No Drawings

TOPICAL STEROID CREAM FORMULATIONS

BACKGROUND OF THE INVENTION

Topical corticosteroids, as a class, demonstrate anti-inflammatory, anti-pruitic and vasoconstrictive actions. They are generally used to relieve the redness, swelling, itching and discomfort of psoriasis, atopic dermatitis and other pathologies of the skin. While the mechanisms of the anti-inflammatory effects are unclear, there appears to be a correlation between the therapeutic effects of these compounds and their vasoconstrictive potencies. Vasoconstrictor assays have been used to compare and predict the relative therapeutic potencies of the drugs in this class (Goodman and Gilman's, "The Pharmacological Basis of Therapeutics", Chapter 25, Tenth Edition).

Commercially, topical steroid products are available as creams, lotions and ointments. U.S. Pat. No. 3,892,856 describes the use of corticosteroids dissolved in polyethylene glycol and emulsified into an oleaginous bases. However, because of the undesirably low solubility of corticosteroids in such vehicles, higher levels of steroids are necessary in these topical products and therefore the costs have been higher and also their cosmetic elegance has been adversely affected.

Mometasone Furoate is a steroid having the chemical name, 9(alpha), 21-Dichloro-11(beta), 17-dihydroxy-16(alpha)-methylpregna-1,4-diene-3,20 dione 17-(2-furoate), the empirical formula $C_{27}H_{30}Cl_2O_6$, and a molecular weight of 521.4. Mometasone furoate is a fine white powder that is insoluble in water, slightly soluble in octanol, and moderately soluble in ethyl alcohol.

The exceptionally poor solubility of mometasone furoate has delayed the development of efficacious, economic and cosmetically elegant topical formulation. U.S. Pat. No. 4,808,610 describes the poor solubility and efficacy of oleaginous topical creams that have mometasone fuorate dissolved into propylene glycol. Additionally, the patent makes reference to a skin irritating effect of certain mometasone fuorate/propylene glycol formulations.

Surprisingly, we have been able to develop a mometasone fuorate cream that is topically effective and non-irritating to the skin. The cream is stable, has an effective biological activity and was found to be non-irritating to the skin when applied. The cream is an oleaginous, occlusive cream with propylene glycol.

SUMMARY OF THE INVENTION

The present invention provides for a water-washable, stable cream that carries a biologically effective amount of the steroid, mometasone furoate. This cream is non-irritating to the skin. The oleaginous, occlusive base for the cream is white petrolatum, containing mometasone furoate partially solubilized in propylene glycol and water. The cream consists of a balanced amount of lipophilic and hydrophilic surfactants and optionally, preservatives, fragrances and stiffening agents.

In particular, this invention provides for a topical cream pharmaceutical composition in the form of an water-in-oil emulsion containing mometasone fuorate and a base comprising (a) a propylene glycol; (b) water; (c) white petrolatum; (d) white wax; (e) stearyl alcohol; (f) a lipophilic surfactant having a HLB value of less than 6; (g) a hydrophilic surfactant having a HLB value of greater than 10; (f) a starch and a whitening agent. The viscosity of the cream is from about 400,000 to about 900,000 centipoise, more particularly the viscosity is from about 650,000 to about 820,000 centipoise The invention provides for an aesthetically pleasing, efficacious skin cream that contains 0.1% mometasone fuorate in the following formulation:
 a) 0.10 percent Mometasone Furoate;
 b) 22.50 percent propylene glycol;
 c) 2.59 percent water;
 d) 3 percent white wax;
 e) 6 percent of propylene glycol stearate;
 f) 1.35 percent of ceteareth-20;
 g) 2.0 percent titanium dioxide;
 h) 10 percent aluminum starch octenylsuccinate;
 i) 51.8 percent white petrolatum; and
 j) sufficient phosphoric acid to adjust the pH of the water
  wherein said composition has a viscosity of about 650,000 to about 825,000 centipoise.

DESCRIPTION OF THE INVENTION

The vehicle used to deliver topical drug products can play an important role in the efficacy and stability of the product. The relative insolubility of mometasone furoate makes the vehicle of particular importance in the development of this formulation. Generally topical cream formulations allow easy application of the product on the skin without leaving an oily residue.

The white petrolatum base of the formulations has an aqueous phase comprising water and an amount of propylene glycol sufficient to partially solubilize the mometasone fuorate. Water-in-oil formulations use surfactants to provide a physically and chemically stable product. Long term stability is an important consideration in the commercialization of a product. The amount of surfactant in the above compositions range from about 0.1 to about 10 wt % of the total composition. In practice, combinations of surfactants (emulsifiers) rather than single agents are used most frequently. The formulation described herein utilizes a combination of surfactants that are relatively lipophilic with some that are relatively hydrophilic. The HLB is hydrophilic/lipophilic balance system which assigns surface-active agents a numerical value which represents a relative hydrophilic or lipophilic property. The theoretical values of HLB range from 1 to approximately 50. The more hydrophilic emulsifiers have HLB values greater than 10, while the more lipophilic emulsifiers have HLB values from 1 to 10.

The relatively lipophilic, non-ionic surfactants of the present invention are the long-chain fatty acids and their water-insoluble derivatives and have HLB values of less than 6. These include (1) fatty alcohols; (2) glyceryl esters; and (3) fatty acid esters of fatty alcohols and other alcohols. To increase the water solubility of these compounds and to form the second group of nonionic agents, polyoxyethylene groups are added through an ether linkage with one of their alcohol groups. The present invention provides for the preferred lipophilic emulsifier, propylene glycol stearate. Other acceptable lipophilic emulsifiers for use in the cream include ethylene glycol monolaurate, ethylene glycol monostearates, propylene glycol monolaurate, glycerol stearate and glyceryl monoricinolate.

The relatively hydrophilic surfactant of the present invention include the preferred Ceteareth-20 and other anionic emulsifiers that have HLB values of greater than 10. Other acceptable anionic, hydrophilic emulsifiers for use in the cream include polyethylene glycol monolaurate, polyethylene glycol distearate, polyoxyethylene cetyl alcohol, polyoxyethylene sorbitan monostearate and polyoxyethylene sorbitan monooleate and polysorbate 80.

Other suitable combinations of hydrophilic and lipophilic surfactants can also be used to serve as the emulsifying system for this invention. The carefully balanced lipophilic and hydrophilic emulsifying agents are used to stabilize the dispersed particles of active agent in the emulsion. In addition to the active ingredient, pharmaceutically acceptable adjuvants, stabilizers, preservatives, whiteners, buffers and surfactants are used in the formulation of this invention.

The mometasone fuorate cream described herein has biological efficacy, and is non-irritating to the skin. The formulation can be used for the topical treatment of dermatological disorders such as contact and allergic dermatitis, eczema and psoriasis. The method of using the cream is by applying it to completely cover the affected area, forming an occlusive barrier. The usual frequency of application is once daily, although adequate maintenance therapy for some patients may be achieved with less frequent application. The formulation of the present invention can be used for administration to warm-blooded animals, including man.

The formulation of the present invention comprises:
a) 1.0 to 5.0 percent Water Purified USP;
b) 0.01 to 0.25 percent Mometasone Furoate;
c) 20 to 30 percent Propylene Glycol NF;
d) 40 to 70 percent White Petrolatum USP;
e) 2.0 to 10.0 percent White Wax NF;
f) 4 to 12 percent of a lipophilic emulsifier with an HLB value of less than 6;
g) 0.7 to 4 percent of a hydrophilic emulsifier with an HLB value of greater than 10;
h) 0.2 to 2.0 percent Titanium Dioxide USP;
i) 5 to 20 percent of a talc like substance; and
j) to 5.0 percent of a whitening agent.

Sufficient acid is added to adjust the pH of the purified water; charged as a 10% w/w solution. Examples of acids which can be utilized in the cream formulation are phosphoric acid, hydrochloric acid, acetic acid, and the like. The preferred acid is phosphoric acid.

Another composition comprises:
a) 2.59 percent Water Purified USP;
b) 0.01 percent phosphoric acid;
c) 0.1 percent Mometasone Furoate;
d) 22.5 percent Propylene Glycol NF;
e) 51.8 percent White Petrolatum USP;
f) 3.0 percent White Wax NF;
g) 6.0 percent of propylene glycol stearate;
h) 0.65 percent of a Ceteararth-20;
i) 2.0 Titanium Dioxide USP; and
j) 10 percent of aluminum starch octenylsucinate The mometasone cream formulations of the present invention is made using standard manufacturing procedures by thoroughly mixing the ingredients at ambient or elevated temperatures. The mometasone furoate is dispersed in a portion of the propylene glycol and added to the oil phase. The ingredients are thoroughly mixed so that the product is homogeneous. Processing equipment suitable for preparing the cream are known in the art and include colloid mills, homogenizers, roller mills, propeller mixers and the like.

The cream of the present invention has a viscosity of from about 400,000 to about 900,000 centipoise, more particularly the bulk material viscosity ranged from about 617,000 to about 824,000 centipoise and the final mometasone cream viscosity was from about 650,000 to about 825,000 centipoise. Viscosity was measured at 25° C. using a Brookfield Viscometer (RV series) Heliopath Stand, "F" T-Spindle (1-10 RPM) (Brookfield Engineering Labs, Inc., Stoughton, Mass.). This viscosity is considerably higher than the currently marketed mometasone furoate creams (Elocon®) which has a viscosity of approximately 200,000 to 300,000 centipoise using a Brookfield Viscometer with a D t-spindle at 5 rpm. The higher viscosity of the cream may be advantageous in that it provides for a greater occlusive barrier, and better adherence to the skin surface.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

EXAMPLE 1

An anti-inflammatory topical cream having 0.1% of the corticosteriod mometasone fuorate was prepared in the following manner. White petrolatum, white wax, stearyl alcohol, propylene glycol stearate and ceteraeth-20 were added to a Brogli Mixing Vessel. This phase was melted by heating to 80° C.±5° C. The agitator speed was adjusted to 30 rpm and aluminum starch octenylsuccinate was added to the mixing vessel through the top port while stirring. The temperature was adjusted to 70° C.±5° C. and stirring was continued for 5 to 10 minutes. The batch was then cooled to 50° C.±2° C. while stirring at 35±4 rpm using to 35° C.±2° C. cooling water.

In another stainless steel container, propylene glycol and mometasone furoate were added together and stirred until the mometasone furoate is wetted. The propylene glycol mixture was then homogenized at a speed of 3,000±500 RPM for 5 to 15 minutes until a uniform dispersion was formed. Titanium dioxide was added to the mixture and stirred to wet the titanium dioxide. The mixture was homogenized at a speed of 3,300±250 RPM for a further 5 to 15 minutes, until a uniform dispersion was formed.

The titanium dioxide, propylene glycol, mometasone furoate mixture was added to the contents of the Brogli Mixing Vessel, and the temperature was maintained at 50° C.

+2° C. for an additional 5 to 15 minutes. The agitator speed was adjusted to 20±5 rpm, and the batch cooled to 30° C.±2° C. using 18° C.±2° C. cooling water. The agitator speed was adjusted to 18±5 rpm, and the batch cooled to 25° C.±2° C. using 18° C.±2° C. cooling water. The agitator was turned off and the batch removed to a container.

The composition of the final cream is given in Table I below:

TABLE I

Final Formulation of Mometasone Furoate Cream

| Ingredient | % of Formulation (w/w) |
| --- | --- |
| Mometasone Furoate Cream | 0.1 |
| Purified Water | 2.59 |
| Phosphoric Acid | 0.01 |
| Propylene Glycol | 22.50 |
| White Wax | 3.00 |
| Stearyl Alcohol | 1.35 |
| Propylene Glycol Stearate | 6.00 |
| Ceteareth-20 | 0.65 |

TABLE I-continued

Final Formulation of Mometasone Furoate Cream

| Ingredient | % of Formulation (w/w) |
|---|---|
| Aluminium Starch Octenylsuccinate | 10.00 |
| Titanium Dioxide | 2.00 |

EXAMPLE 2

Mometasone furoate's well-known vasoconstrictive effect was used as the basis for the study of bioequivalence and efficacy. Additionally, propylene glycols effect on the skin was studied. A one-period, randomized, vasoconstrictor study was done to compare the bioavailability of the innovative 0.1% mometasone furoate cream ("Test Formulation") to the commercially available mometasone cream 0.1% ("Control Formulation") (ELOCON®, Schering-Plough Corporation, Kenilworth, N.J.). The formulation for this cream is disclosed in U.S. Pat. No. 4,808,610, and uses hexylene glycol to dissolve the mometasone furoate.

54 subjects were chosen for participation in the study. The subjects were healthy, non-tobacco using (for 30 days prior to dosing), females in the age range of 18-47 years, and were within 20% of their ideal weight. Potential participants were screened to determine blanching response to the control cream. All subjects were selected based on a demonstrated blanching response (at least a 1 on a 0 to 3 scale), and the absence of any clinically significant finding on the medical history and clinically assessment. Selected subjects had no history of allergy or hypersensitivity to any corticosteroids or to any topical products. The selected subjects had no skin condition or coloration, which would interfere with the response or assessment of skin blanching. All subjects tested negative on the urine pregnancy test. After meeting qualifying criteria, 34 of the 54 subjects were included in the study. The criteria necessary to qualify for the study was the subjects time dependent response to the control cream. If the subject did not have a time dependent response, they were excluded from the study.

A colorimeter (Chroma Meter CR-300 (Minolta USA)) was used to measure the reflective colors from the skin surface and six high-sensitivity silicon photocells were used by the meter's double-beam feedback system to measure both incident and reflected light. The calorimeter operators assessed the degree of blanching response at each site prior to treatment application and at 0, 2, 4, 6, 8, 10, 12, 20, and 24 after removal. Negative areas under the response curve for the colorimeter assessments were determined from the a-scale reading. The ratio of the mean area under the response curve for the reference 2-hour duration (D2) to that of the 30-minute duration (D1) was calculated for each subject. Subjects whose D2/D1 ration was at least 1.25 were considered qualified for inclusion in the statistical analyses. Locke's Method (Locke, CS; Journal of Pharmacokinet Biopharm 1984: 12:649-55) for calculating confidence intervals was applied to the colorimeter results.

A 10 µl amount of each cream was applied in duplicate to the flexor surface of each subject's forearms and left in place for one hour. This duration time was based on the calorimeter $ED_{50}$ from a previous dose response study. The test cream and the control product were each applied to a total of eight sites on each arm. The degree of vasoconstriction was determined by taking measurements at pre-dose, 0, 2, 4, 6, 8, 10, 12, 20 and 24 hours after treatment removal. The average of duplicate pre-dose readings at each site on each arm was used to normalize the colorimeter readings. colorimeter operators were blinded as to the treatment and duration of application at each site.

Table II summarizes the bioequivalence comparisons for the colorimeter data for the qualifying subjects.

TABLE II

Mean Results for Comparison of Vasoconstrictor Bioequivalence

| Formulations | N | Test Mean | Reference Mean | Ratio (%)[1] | 90% Conf. Interval[2] | |
|---|---|---|---|---|---|---|
| Test Formulation vs. Control Formulation | 34 | 23.9 | 22.4 | 106.6 | 95.7 | 119 |

[1]Ratio percent calculated as: (Test/Reference) × 100%
[2]Confidence interval on the ratio The subjects were monitored throughout the study for any adverse experiences. None of the subjects reported any adverse events during, including skin irritation, throughout the study.

Based on the calorimeter results, the experimental formulation is bioequivalent to the control, commercially available formulation.

What is claimed is:

1. A topical water-in-oil pharmaceutical cream composition for the treatment of inflammation comprising:
    a) 0.01 to 0.25 percent Mometasone Furoate;
    b) 10 to 30 percent propylene glycol;
    c) 1.0 to 5 percent water;
    d) 2.0 to 10.0 percent white wax;
    e) 4.0 to 12.0 percent of a lipophilic surfactant having an HLB value of less than 6;
    f) 0.7 to 4.0 percent of a hydrophilic surfactant having an HLB value of greater than 10;
    g) 0.2 to 2.0 percent Titanium dioxide;
    h) 5.0 to 20.0 percent aluminum starch octenylsuccinate;
    i) 40 to 70 percent white petrolatum; and
    j) sufficient acid to adjust the pH of the water wherein said composition has a viscosity of about 400,000 to about 900,000 centipoise,
    wherein the cream composition is effective for treating inflammation.

2. The topical pharmaceutical composition of claim 1 wherein the lipophilic surfactant is selected from the group consisting of propylene glycol stearate, ethylene glycol monolaurate, ethylene glycol monostearate, propylene glycol monolaurate and glyceryl monoricinolate.

3. The topical pharmaceutical composition of claim 1 wherein the hydrophilic surfactant is selected from the group consisting of stearyl alcohol and ceteareth-20, polyethylene glycol monolaurate, polyethylene glycol distearate, polyoxyethylene cetyl alcohol, polyoxyethylene sorbitan monostearate and polyoxyethylene sorbitan monooleate.

4. The topical pharmaceutical composition of claim 1 wherein the acid utilized to adjust the pH of the water is selected from the group consisting of phosphoric acid, hydrochloric acid, and acetic acid.

5. A topical water-in-oil pharmaceutical cream composition for the treatment of inflammation comprising:
    a) 0.10 percent Mometasone Furoate;
    b) 22.50 percent propylene glycol;
    c) 2.59 percent water;
    d) 3 percent white wax;

e) 6 percent of propylene glycol stearate;
f) 1.35 percent of ceteareth-20;
g) 2.0 percent Titanium dioxide;
h) 10 percent aluminum starch octenylsuccinate;
i) 51.8 percent white petrolatum; and
j) sufficient phosphoric acid to adjust the pH of the water to wherein said composition has a viscosity of about 650,000 to about 825,000 centipoise,
wherein the cream composition is effective for treating inflammation.

6. A method for treating a patient suffering from inflammation of the skin, comprising:
applying a layer of the topical water-in-oil pharmaceutical cream of claim 1 to the inflamed skin of the patient; and
allowing the layer of the topical water-in-oil pharmaceutical cream to remain on the skin for a duration effective to reduce the inflammation.

7. The method of claim 6, wherein the topical water-in-oil pharmaceutical cream does not irritate the skin.

8. A method for treating a patient suffering from inflammation of the skin, comprising:
applying a layer of about 10 μl of the topical water-in-oil pharmaceutical cream of claim 1 to the inflamed skin of the patient; and
allowing the layer of the topical water-in-oil pharmaceutical cream to remain on the skin for about 1 hour.

9. The method of claim 8, wherein the topical water-in-oil pharmaceutical cream does not irritate the skin during the time the topical water-in-oil pharmaceutical cream remains on the skin.

* * * * *